(12) United States Patent
Hou et al.

(10) Patent No.: US 11,352,392 B2
(45) Date of Patent: Jun. 7, 2022

(54) ARTIFICIALLY SYNTHESIZED PEPTIDE H-473 AND USE THEREOF

(71) Applicant: CHINA WEST NORMAL UNIVERSITY, Nangchong (CN)

(72) Inventors: Yiling Hou, Nangchong (CN); Wanru Hou, Nangchong (CN); Xiang Ding, Nangchong (CN)

( * ) Notice: Subject to any disclaimer, the term of this patent is extended or adjusted under 35 U.S.C. 154(b) by 15 days.

(21) Appl. No.: 17/049,907

(22) PCT Filed: Jan. 16, 2019

(86) PCT No.: PCT/CN2019/072013
§ 371 (c)(1),
(2) Date: Oct. 22, 2020

(87) PCT Pub. No.: WO2020/133605
PCT Pub. Date: Jul. 2, 2020

(65) Prior Publication Data
US 2021/0230223 A1    Jul. 29, 2021

(30) Foreign Application Priority Data
Dec. 27, 2018    (CN) .......................... 201811612034.0

(51) Int. Cl.
*C07K 7/06* (2006.01)
*A61K 38/00* (2006.01)

(52) U.S. Cl.
CPC ................ *C07K 7/06* (2013.01); *A61K 38/00* (2013.01)

(58) Field of Classification Search
None
See application file for complete search history.

(56) References Cited

U.S. PATENT DOCUMENTS 5,595,756 A * 1/1997 Bally .................. A61K 9/1272
264/4.1

OTHER PUBLICATIONS

Can Dementia be Prevented 2021 five pages. (Year: 2021).*
How Can You Prevent age related Macular Degeneration 2021 three pages. (Year: 2021).*
Zugazagoitia et al, Current Challenges in Cancer Treatment, Clinical Therapies, vol. 38, (2016), pp. 1551-1566 (Year: 2016).*
Sporn et at, "Chemoprevention of Cancer," Carcinogenesis, vol. 21 (2000), 525-530 (Year: 2000).*

* cited by examiner

*Primary Examiner* — Thomas S Heard

(57) ABSTRACT

The invention discloses an artificially synthesized peptide H-473 and use thereof. The peptide H-473 has an amino acid sequence of RGLRGLR, a molecular weight of 827 Da and a PI of 12.30. The invention further discloses use of the peptide H-473 in anti-cancer, anti-senile dementia, analgesia and the like. The peptide H-473 provides scientific basis and direction for research and development of anti-cancer, anti-asthma, anti-senile dementia and analgesia, provides a valuable resource for studying mechanisms of anti-cancer, anti-asthma, anti-senile dementia, analgesia and anti-psoriasis, and provides a new direction for researching novel means for anti-cancer, anti-asthma, anti-senile dementia, analgesia, anti-psoriasis and anti-age-related macular degeneration (AMD).

9 Claims, 2 Drawing Sheets

Specification includes a Sequence Listing.

SEQUENCE LISTING

```
<160> NUMBER OF SEQ ID NOS: 1

<210> SEQ ID NO 1
<211> LENGTH: 7
<212> TYPE: PRT
<213> ORGANISM: Artificial Sequence
<220> FEATURE:
<223> OTHER INFORMATION: H-473

<400> SEQUENCE: 1

Arg Gly Leu Arg Gly Leu Arg
1               5
```

ARTIFICIALLY SYNTHESIZED PEPTIDE H-473 AND USE THEREOF

RELATED APPLICATIONS

This application is a United States National Stage Application filed under 35 U.S.C 371 of PCT Patent Application Serial No. PCT/CN2019/072013, filed Jan. 16, 2019, which claims Chinese Patent Application Serial No. CN201811612034.0, filed Dec. 27, 2018, the disclosure of all of which are hereby incorporated by reference in their entirety.

FIELD OF THE INVENTION

The invention belongs to the technical field of biological medicines, and relates to an artificially synthesized peptide H-473 and use thereof, in particular to use of H-473 in preparation of medicaments for anti-cancer, anti-senile dementia, anti-asthma, analgesia, anti-psoriasis, anti-age-related macular degeneration and the like.

SEQUENCE LISTING

This application contains a Sequence Listing in computer readable form. The computer readable form is incorporated herein by reference. The name of the ASCII text file is "SQL", with a file size of 1 kb and a creation date of Mar. 3, 2022.

BACKGROUND OF THE INVENTION

To perform their biological functions, proteins usually interact with other proteins to reflect their functional effects, i.e., protein interaction is a basic event of life activities at the molecular level. Monoclonal antibodies and small molecule drugs of specific structures, including small molecule peptides, can inhibit these interactions. It is also known in the biomedical field as targeted therapy. Monoclonal antibody drugs have not only achieved good results in the treatment of tumors, but also achieved some effects in the treatment of other diseases, for example, omalizumab, by binding to free IgE, can significantly reduce the level of free IgE, block the binding of IgE to mast cells and basophils, prevent the release of inflammatory mediators, significantly improve the symptoms, lung function and quality of life of asthmatic patients, reduce the number of exacerbations of asthma, reduce the dosage of glucocorticoids, is safe to use, and has good tolerance; rituximab also has a good therapeutic effect on rheumatoid and systemic lupus erythematosus; and infliximab can alleviate clinical symptoms in patients with rheumatoid arthritis, such as pain, morning stiffness, joint swelling and the like, by up to 60%. Other studies have shown that infusion of infliximab can rapidly and significantly alleviate the symptoms of joints and lesions in patients with refractory psoriasis and arthritis; and infliximab further has a good therapeutic effect on Crohn's disease, ulcerative colitis, alcoholic liver disease and other digestive system diseases, and is safe within the recommended therapeutic range. Ranibizumab can be used to treat wet (neovascular) age-related macular degeneration (AMD). These examples illustrate that certain drugs have multi-target therapeutic properties.

According to a principle that spatial structure and functional characteristics of proprotein molecules will be changed after protein molecules are affected by other molecules, in the invention, based on analysis of molecular structure and functional sites of proteins such as related receptors in a molecular pathway of cancer (FZDs, ITG, FGFR, ErBB2, PDGFR, IGFR, KIT, FGFR, HGFR, TRK and the like); related receptors in molecular pathways of bronchial asthma and chronic inflammatory (TLR4, TLR1, TLR5, TLR6 and the like); opioid receptors, senile dementia-related acetylcholinesterase, psoriasis-related factors and age-related macular degeneration (AMD) related factors and the like, a multi-target therapeutic small molecule peptide was designed to interfere with the functions of these receptors, cytokines and enzyme molecules to achieve a purpose of treating related diseases. The inventor has synthesized peptide H-473 and, to date, provided biomedical efficacy of the peptide H-473 in anti-cancer, anti-asthma, anti-senile dementia, analgesia, and treatment of psoriasis and age-related macular degeneration (AMD), and uses thereof.

SUMMARY OF THE INVENTION

The invention aims to provide an artificially synthesized peptide H-473 and use thereof, and to reveal application prospects of the artificially synthesized peptide H-473 in active effects in anti-cancer, anti-asthma, anti-senile dementia, analgesia and treatment of psoriasis.

In order to achieve the above technical purposes, the invention is specifically realized by the following technical schemes:

An artificially synthesized peptide H-473, wherein the peptide H-473 has an amino acid sequence of RGLRGLR, a molecular weight of 827 Da, and a PI of 12.30. The peptide is single-stranded and has no chemical bond modification.

The peptide H-473 has little inhibitory effect on growth of normal human liver Chang Liver cells (only weak growth inhibition effect or weak growth promotion effect), while has remarkable inhibitory effect on growth of human gastric cancer MGC-803 cells and human pancreatic cancer cfpac-1 cells.

In the invention, by constructing a mouse acetylcholinesterase animal model and combining the constructed standard curve of acetylcholinesterase, the acetylcholinesterase of a brain tissue of each experimental group was measured and the expression level of acetylcholinesterase in brain cells of each experimental group was calculated, as a result, the peptide H-473 had an inhibition rate of 55.6% and an interference rate of 43.8% on the expression of acetylcholinesterase in brain tissue.

The peptide H-473 has remarkable anti-asthma activity. According to a mouse analgesic model, analgesic effect of the peptide H-473 on mice was observed. The peptide H-473 obviously reduced the number of acetic acid-induced writhing response in the mice, and each dose group had an obvious analgesic effect on the acetic acid-induced pain.

Meanwhile, the peptide H-473 can significantly down-regulate the expression of proteins related to occurrence and development of psoriasis, such as CARMA, VEGF, IL6, IL8, IL1-R, TNF-R1, IL17RA, IL12, IL12R and the like at molecular, cellular and animal levels, and is expected to be a potent anti-psoriatic drug.

The peptide H-473 can significantly down-regulate expression of VEGF in cells, effectively inhibit the biological activity of VEGF, effectively interfere with VEGF related receptors, such as VEGFR, PDGFR, etc., and finally achieve inhibition of vascular proliferation and achieve a purpose of anti-age-related macular degeneration (AMD).

In another aspect of the invention, the invention provides use of the peptide H-473 in a medicament for preventing and/or treating cancer, including human gastric cancer and human pancreatic cancer.

In another aspect of the invention, the invention provides use of the peptide H-473 in a medicament for preventing and/or treating senile dementia.

In another aspect of the invention, the invention provides use of the peptide H-473 in a medicament for preventing and/or treating pain, including burns and scalds, external force injury, frostbite, inflammatory pain, neuropathic injury and pain caused by other reasons.

In another aspect of the invention, the invention provides use of the peptide H-473 in a medicament for preventing and/or treating asthma.

In another aspect of the invention, the invention provides use of the peptide H-473 in a medicament for preventing and/or treating psoriasis.

In another aspect of the invention, the invention provides use of the peptide H-473 in a medicament for preventing and/or treating age-related macular degeneration (AMD).

One or more pharmaceutically acceptable auxiliary materials can be added into the above medicament, including conventional diluents, stabilizers, fillers, excipients, binders, wetting agents, absorption promoters, surfactants, lubricants and the like in the pharmaceutical field.

The medicament can be prepared into various forms such as injections, freeze-dried preparations, implants, tablets or granules. The medicaments in the above various dosage forms can be prepared according to conventional methods in the pharmaceutical art.

The invention has the beneficial effects that:

The peptide H-473 is a small molecule peptide, is easy to prepare, has a low preparation process cost, and has a good application value in anti-cancer, anti-asthma, anti-senile dementia, analgesia and anti-psoriasis. Studies have shown that the peptide H-473 has an inhibition rate of up to 51.9% on growth of human gastric cancer MGC-803 cells; an inhibition rate of up to 48.8% on growth of human pancreatic cancer cfpac-1 cells; an inhibition rate of up to 64.1% on human gastric cancer MGC-803 xenograft tumors in nude mice; an inhibition rate of up to 68.04% on human pancreatic cancer cfpac-1 xenograft tumors in nude mice; an inhibition rate of 55.6% on expression of acetylcholinesterase in brain tissue; an interference rate of 43.8% on expression of acetylcholinesterase in brain tissue; and inhibition rate of 81.95% and 95.11% on acetic acid-induced writhing response in mice at doses of 0.5 mg/kg and 1 mg/kg, respectively. The peptide H-473 provides a valuable resource and direction for research on novel anti-cancer, anti-asthma, anti-senile dementia, analgesic, anti-psoriasis and anti-age-related macular degeneration (AMD) drugs.

DETAILED DESCRIPTION OF THE INVENTION

Figure 1:
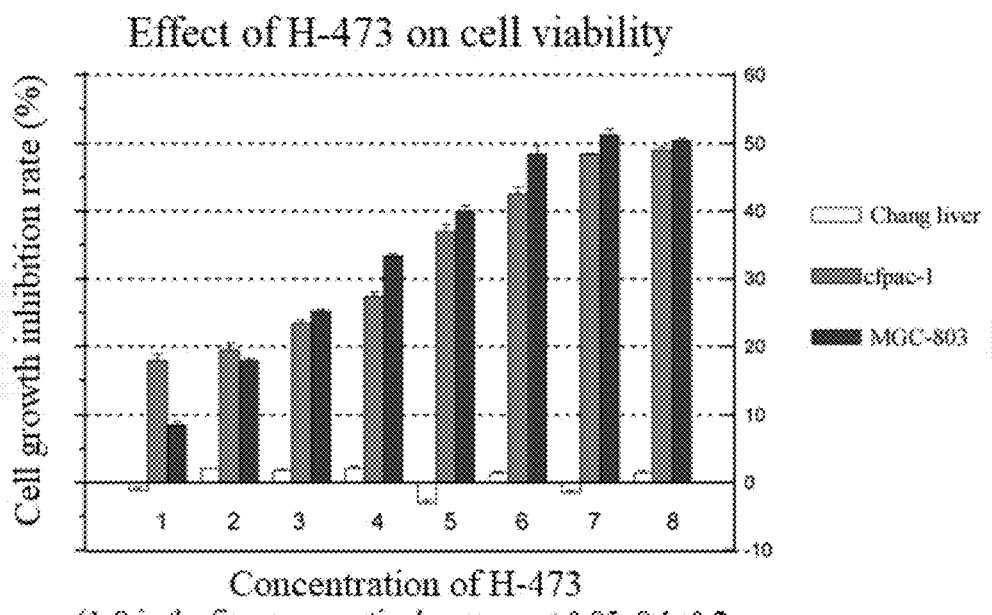
FIG. 1 is a graph showing the effect of the peptide H-473 on cell viability.

The technical schemes of the invention will be clearly and completely described below with reference to specific examples of the invention. Obviously, the described examples are only a part of the examples of the invention, rather than all. Based on the examples of the invention, all other examples obtained by a person skilled in the art without involving any inventive labor shall fall within the scope of the invention.

Example 1 Construction of Cell Model and Validation of Anti-Cancer Effect

1. Cell Model
1.1 Materials and Methods
1.1.1 Materials
1.1.1.1 Cell lines: human normal liver Chang Liver cells, human gastric cancer MGC-803 cells, human pancreatic cancer cfpac-1 cells, the above cell lines are all commercially available.
1.1.1.2 Reagents: RPMI1640 powder (purchased from Gibco, USA), fetal bovine serum (purchased from Sijiqing Bioproducts, China), and diabodies (penicillin and streptomycin, purchased from Gibco).
1.1.1.3 H-473: amino acid sequence: RGLRGLR, molecular weight: 827 Da; PI: 12.30, and purity: 98.12%.
1.1.2 Method
1.1.2.1 Cell Culture Human normal liver Chang Liver cells, human gastric cancer MGC-803 cells, human pancreatic cancer cfpac-1 cells were cultured in RPMI-1640 complete medium at pH 7.4 containing 10% inactivated fetal bovine serum (FBS), 100 U/ml penicillin and 100 µg/ml streptomycin in an incubator with 5% $CO_2$ at 37° C., respectively.

1.1.2.2 MTT Assay for Cell Viability

After trypsinization, the number of Chang Liver cells, MGC-803 cells and cfpac-1 cells in the logarithmic growth phase were adjusted to $1\times10^5$ cells/mL. The cells were inoculated in a 96-well plate, 200 µL/well, and incubated in a $CO_2$ incubator with 5% $CO_2$ and saturated humidity at 37° C. until a bottom of the well was covered with a single layer of cells (96-well flat bottom plate). Then, H-473 was added to final concentrations of 0.05, 0.1, 0.2, 0.5, 0.8, 1.5, 3.0 and 6.0 µg/ml respectively. Six replicate wells were set up, and the blank group contained RPMI1640 medium without cells. After culturing for 24, 36 and 48 hours in the $CO_2$ incubator, the 96-well plate was taken out, 10 µL of MTT (5 mg/mL) solution was added, the cells were cultured for another 4 h, then 150 µL of dimethyl sulfoxide (DMSO) was added, and the 96-well plate was shaken for 10 min. After blue-violet crystals were completely dissolved, absorbance (OD) value of each well was measured with a microplate reader at a wavelength of 490 nm, and inhibition rate (%) of H-473 on various types of cells at different concentrations was calculated (In this example, H-473 was directly added to well-grown cancer cells to observe results. In clinical practice, protein or peptide biological drugs are usually in the form of injections, injected intramuscularly or injected intravenously). Cell growth inhibition rate was calculated according to the following formula:

Cell growth inhibition rate=(1-A experimental group/A control group)×100%.

On the basis of the above experiments, MGC-803 cells, cfpac-1 cells and Chang Liver cells (H-473 had the best growth inhibitory effect on these cells) were selected for comparative experiments, the culture time was 36 hours, and statistical data were obtained. The specific methods and procedures were the same as above.

1.2 Results

This example adopted the MTT assay, and detection results showed that: at 36 h, H-473 at different concentrations had little inhibitory effect on the growth of Chang Liver cells (only weak growth inhibition or weak growth promotion), but had remarkable inhibitory effect on the growth of MGC-803 cells and cfpac-1 cells. As can be seen from FIG. 1, H-473 has a dose-dependent growth inhibition rate on MGC-803 cells and cfpac-1 cells. It was found that H-473 had a cell growth inhibition rate of 51.9% on MGC-803 cells at a concentration of 3.0 μm/ml, and a cell growth inhibition rate of 48.8% on cfpac-1 cells at a concentration of 6.0 μm/ml.

Example 2 Pharmacodynamic Experiment on Human Gastric Cancer MGC-803 Xenograft Tumor in Nude Mice 2.1 Experimental Objective:

According to the requirements of "Guiding Principles of Pharmacodynamics of Antitumor Drugs" and "Technical Guiding Principles for Non-clinical Research of Cytotoxic Antitumor Drugs", H-473 was tested for its inhibitory effect and intensity on the growth of MGC-803 xenograft tumors.

2.2 Test Sample:

Peptide H-473.

Preparation method: 1 mg of H-473 was dissolved in 1 ml of physiological saline, and then diluted in multiples to obtain a peptide solution with desired concentration.

2.3 Control Drug:

Interleukin-2.

Manufacturer: Beijing Shuanglu Pharmaceutical Co., Ltd., China.

Batch Number: 20120824.

Preparation method: an interleukin-2 solution of 20,000 IU/ml in physiological saline was prepared prior to dosing.

2.4 Groups and Dosage Regimen:

Model control group: physiological saline, 0.1 ml/10 g, once a day for 10 times.

Interleukin-2: 20,000 IU/ml interleukin-2 solution, injected into tail vein, 0.1 ml/10 g, once a day for 10 times.

Peptide H-473-1μg/kg group: 0.1 μg/ml peptide H-473 solution, injected into the tail vein, 0.1 ml/10 g, once a day for 10 times.

2. 5 Test Animals:

Source, germline, and strain: BALB/c nude mice, provided by Laboratory Animal Center, Academy of Military Medical Sciences, China.

Laboratory animal production license: SCXK (Military) 2012-004.

Certificate number: 0039642.

Laboratory animal use license: SYXK (SU) 2011-0036.

Day Age: 4-5 w.

Body weight: 18-22 g.

Gender: male.

Number of animals: 8 in each group, 24 in total.

2.6 Experimental Method:

2.6.1 Preparation of Model

The cultured MGC-803 cell suspension was collected at a concentration of $1\times10^7$ cells/ml and inoculated subcutaneously in the right axilla of nude mice, 0.1 ml/mouse.

2.6.2 Grouping and Dosing

Diameters of the xenograft tumors in nude mice were measured with a vernier caliper. 8 days after inoculation, the animals were randomized into groups with 8 in each group when the tumors grew to 100-150 mm³. At the same time, each group of nude mice began to be dosed. The dosage regimen can be found in "Groups and dosage regimen". The anti-tumor effect of the test sample was dynamically observed by using a method of measuring tumor diameter. 10 days after dosing, observation was continued for 4 days, and then the nude mice were sacrificed, and tumor mass was surgically removed and weighed.

2.6.3 Observation Indicators

Tumor volume (TV) was calculated according to the following formula: $TV = \frac{1}{2} \times a \times b^2$, wherein, a and b represent length and width, respectively.

Relative tumor volume (RTV) was calculated according to the measured results according to the following formula: $RTV = V_t/V_0$, wherein, $V_0$ is tumor volume measured when the animals are divided into cages and dosed (i.e., $d_0$) and $V_t$ is tumor volume at each measurement.

Evaluation indicator of anti-tumor activity: relative tumor proliferation rate T/C (%) was calculated according to the following formula:

$$T/C(\%) = \frac{T_{RTV}}{C_{RTV}} \times 100$$

wherein, $T_{RTV}$: RTV of treatment group; and $C_{RTV}$: RTV of model group.

Evaluation indicator of antitumor activity: tumor growth inhibition rate (%) was calculated according to the following formula:

$$\text{Tumor growth inhibition rate} = \frac{\text{Average tumor weight of dosing group} - \text{Average tumor weight of model group}}{\text{Average tumor weight of model group}} \times 100\%$$

2.6.4 Statistical Processing

Mean values were expressed as X±SD, inter-group analysis was statistically processed using t-test, and results were statistically analyzed using SPSS (Staffstical Package for the Social Science) 17.0.

Figure 2:
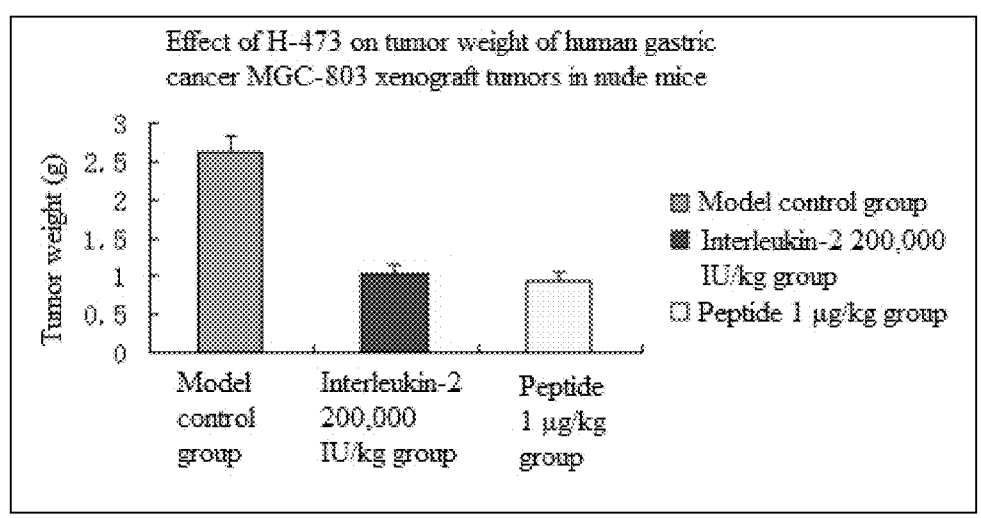
FIG. 2 is a graph showing the effect of the peptide H-473 on growth of human gastric cancer xenograft tumors in nude mice in Example 2.

2.7 Experimental Results and Conclusions:

In this example, a xenograft tumor model of MGC-803 in nude mice was constructed, and the anti-tumor activity of H-473 at a concentration of 1 μg/kg was evaluated by using this model. The experimental results were as follows: tumor inhibition rate of H-473 was 64.1%, and under the same conditions, tumor inhibition rate of positive control IL-2 group (200,000 U/kg) was 60.9%. The conclusion is as follows: H-473 has a significant anti-tumor activity at a concentration of 1 μg/kg, and a tumor inhibition rate of >40%, and a significant difference compared with the model group. The experimental results of this example are shown in Table 1. The effect of H-473 on growth of MGC-803 xenograft tumors in nude mice in this example is shown in FIG. 2.

TABLE 1

Inhibitory effect of H-473 on growth of MGC-803 xenograft tumors in nude mice (X ± SD, n = 8)

| Groups | Experimental period (days) | Number of animals At sacrifice (mouse) | Body weight of animals At sacrifice (g) | Tumor weight (g) | Tumor inhibition rate |
|---|---|---|---|---|---|
| Model group | 24 | 8 | 23.37 ± 1.38 | 2.615 ± 0.212 | |
| Interleukin-2 200,000 IU/kg | 24 | 8 | 23.33 ± 1.44 | 1.023 ± 0.121** | 60.9% |
| H-473 group (1 µg/kg) | 24 | 8 | 22.80 ± 0.97 | 0.938 ± 0.130** | 64.1% |

Example 3 Pharmacodynamic Experiment on Cfpac-1 Xenograft Tumor in Nude Mice 3.1 Experimental Objective:

According to the requirements of "Guiding Principles of Pharmacodynamics of Antitumor Drugs" and "Technical Guiding Principles for Non-clinical Research of Cytotoxic Antitumor Drugs", H-473 was tested for its inhibitory effect and intensity on the growth of cfpac-1 xenograft tumors.

3.2 Test Sample:

Peptide H-473.

Preparation method: 1 mg of H-473 was dissolved in 1 ml of physiological saline, and then diluted in multiples to obtain a peptide solution with desired concentration.

3.3 Control Drug:

Interleukin-2.

Manufacturer: Beijing Shuanglu Pharmaceutical Co., Ltd., China.

Batch number: 20131037.

Preparation method: an interleukin-2 solution of 20,000 IU/ml in physiological saline was prepared prior to dosing.

3.4 Groups and Dosage Regimen:

Model control group: physiological saline, 0.1 ml/10 g, once a day for 10 times.

Interleukin-2: 20,000 IU/ml interleukin-2 solution, injected into tail vein, 0.1 ml/10 g, once a day for 10 times.

Peptide H-473-1 µg/kg group: 0.1 µg/ml peptide H-473 solution, injected into the tail vein, 0.1 ml/10 g, once a day for 10 times.

3.5 Test Animals:

Source, germline, and strain: BALB/c nude mice, provided by Laboratory Animal Center, Academy of Military Medical Sciences, China.

Laboratory animal production license: SCXK (Military) 2012-004.

Certificate number: 0018558.

Laboratory animal use license: SYXK (SU) 2011-0036.

Day age: 4-5 w.

Body weight: 18-22 g.

Gender: male.

Number of animals: 8 in each group, 24 in total.

3.6 Experimental Method:

3.6.1 Preparation of Model

The cultured cfpac-1 cell suspension was collected at a concentration of $1 \times 10^7$ cells/ml and inoculated subcutaneously in the right axilla of nude mice, 0.1 ml/mouse.

3.6.2 Grouping and Dosing

Diameters of the xenograft tumors in nude mice were measured with a vernier caliper. 17 days after inoculation, the animals were randomized into groups with 8 in each group when the tumors grew to 100-150 mm³. At the same time, each group of nude mice began to be dosed. The dosage regimen can be found in "Groups and dosage regimen". The anti-tumor effect of the test sample was dynamically observed by using a method of measuring tumor diameter. 10 days after administration, observation was continued for 3 days, and then the nude mice were sacrificed, and tumor mass was surgically removed and weighed.

3.6.3 Observation Indicators

Tumor volume (TV) was calculated according to the following formula: TV=½×a×b², wherein, a and b represent length and width, respectively.

Relative tumor volume (RTV) was calculated according to the measured results according to the following formula: RTV=$V_t/V_0$, wherein, $V_0$ is tumor volume measured when the animals are divided into cages and dosed (i.e., $d_0$) and $V_t$ is tumor volume at each measurement.

Evaluation indicator of anti-tumor activity: relative tumor proliferation rate T/C (%) was calculated according to the following formula:

$$T/C(\%) = \frac{T_{RTV}}{C_{RTV}} \times 100$$

wherein, $T_{RTV}$: RTV of treatment group; and $C_{RTV}$: RTV of model group.

Evaluation indicator of antitumor activity: tumor growth inhibition rate (%) was calculated according to the following formula:

$$\text{Tumor growth inhibition rate} = \frac{\text{Average tumor weight of model group} - \text{Average tumor weight of dosing group}}{\text{Average tumor weight of model group}} \times 100\%$$

3.6.4 Statistical Processing

Mean values were expressed as X±SD, inter-group analysis was statistically processed using t-test, and results were statistically analyzed using SPSS (Staffstical Package for the Social Science) 17.0.

Figure 3:
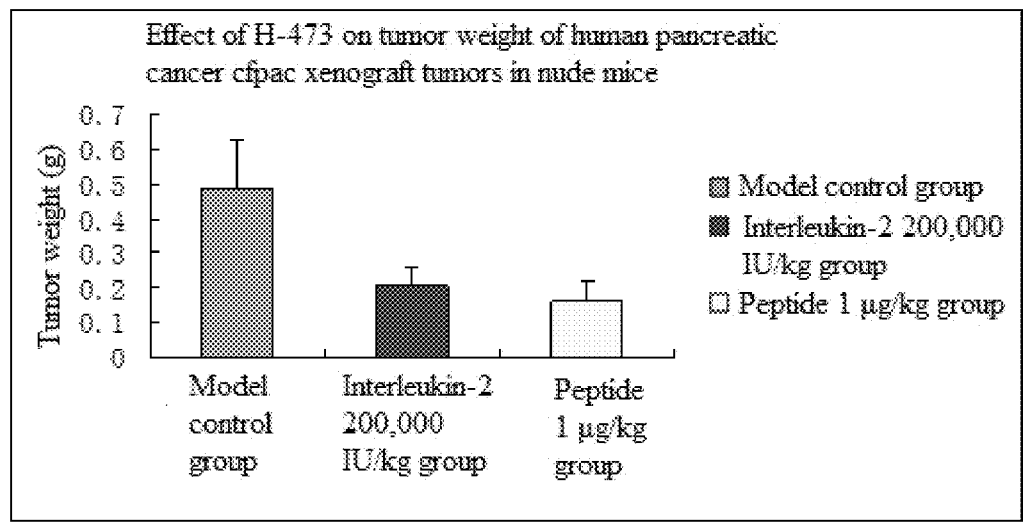
FIG. 3 is a graph showing the effect of the peptide H-473 on growth of human pancreatic cancer xenograft tumors in nude mice in Example 3.

3.7 Experimental Results and Conclusions:

In this example, a xenograft tumor model of cfpac-1 in nude mice was constructed, and the anti-tumor activity of peptide H-473 at a concentration of 1 µg/kg was evaluated by using this model. The experimental results were as follows: tumor inhibition rate of H-473 was 56.1%, and under the same conditions, tumor inhibition rate of positive control IL-2 group (200,000 U/kg) was 68.04%. The conclusion is as follows: H-473 has a significant anti-tumor activity at a concentration of 1 µg/kg, and a tumor inhibition rate of >40%, and a significant difference compared with the model group. The experimental results of this example are shown in Table 2. The effect of H-473 on growth of cfpac-1 xenograft tumors in nude mice in this example is shown in FIG. 3.

TABLE 2

Effect of H-473 on growth of cfpac-1 xenograft tumors in nude mice (X ± SD, n = 8)

| Groups | Experimental period (days) | Number of animals At sacrifice (mouse) | Body weight of animals At sacrifice (g) | Tumor weight (g) | Tumor inhibition rate |
|---|---|---|---|---|---|
| Model group | 24 | 8 | 23.57 ± 1.31 | 0.49 ± 0.0.14 | |
| Interleukin-2 200,000 IU/kg | 24 | 8 | 23.04 ± 1.41 | 0.21 ± 0.0.05** | 56.1% |
| H-473 group (1 μg/kg) | 24 | 8 | 22.91 ± 1.12 | 0.16 ± 0.06** | 68.04% |

Example 4 Acetylcholinesterase Mouse Model Experiment 4.1 Experimental Objective:

Inhibitory and interfering effects of H-473 on acetylcholinesterase expression in brain cells were evaluated.

4.2 Reagents: D-Galactose, Sodium Nitrite, and Animal Brain Tissue Protein Extraction Kit.

4.3 Model Construction:

32 mice were randomized into 4 groups with 8 mice in each group.

Control group: no treatment, normal feeding every day.

Expression inhibition group: each mouse was injected intramuscularly with 200 μg/kg H-473 daily for 30 days.

Model group: each mouse was injected intraperitoneally with 150 mg/kg D-galactose and 120 mg/kg sodium nitrite daily for 30 days.

Interference Group: on the basis of the model group, each mouse was injected intramuscularly with 200 μg/kg H-473 daily for 30 days.

4.4 Sample Collection:

Brain tissue of each group was collected, and the brain tissues of the same weight were mixed together for each group.

The collected brain tissue was immediately treated with liquid nitrogen and equally divided into 3 fractions after treatment, and stored at ultra-low temperature of −80° C.

Brain tissue protein was extracted with an animal brain tissue protein extraction kit.

Expression level of acetylcholinesterase in brain cells of each experimental group was determined by an ELISA kit.

4.5 Data Statistics

Expression inhibition rate was calculated by the following formula:

Expression inhibition rate %=(expression level of control group−expression level of inhibition group)/expression level of control group×100%.

Interference expression rate was calculated by the following formula:

Interference expression rate %=(expression level of model group−expression level of interference group)/expression level of model group×100%.

4.6 Experimental Results.

Figure 4:
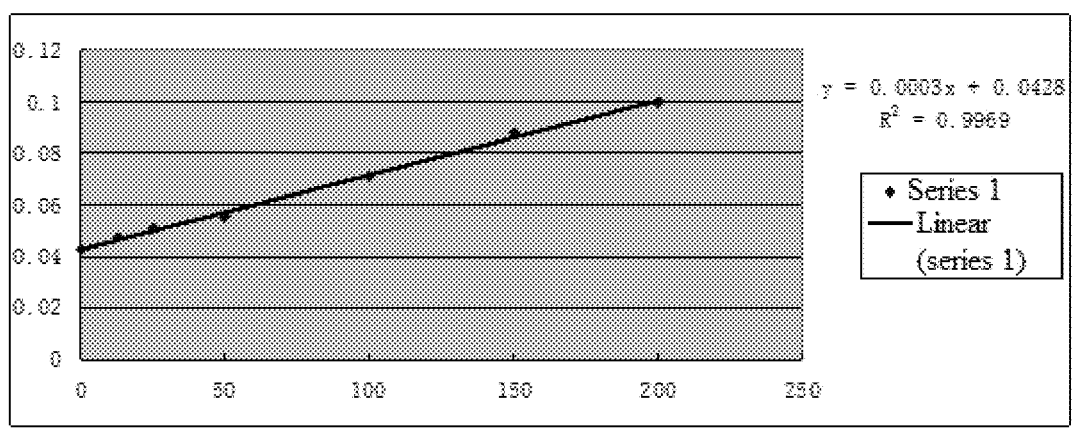
FIG. 4 is a standard curve for acetylcholinesterase.

According to the ELISA kit instructions, a standard curve of acetylcholinesterase was constructed (FIG. 4), acetylcholinesterase in brain tissue of each group was measured, and then expression level of acetylcholinesterase in brain cells of each experimental group was calculated using the standard curve (Table 3). The expression inhibition rate was 55.6% (compared with control group). The interference expression rate was 43.8% (compared with model group). The results showed that: H-473 significantly inhibited the expression of acetylcholinesterase in brain cells.

TABLE 3

Measurements of expression level of acetylcholinesterase in brain tissue of each experimental group (nmol/L).

| Control group | H-473 inhibition group | Model group | H-473 interference group |
|---|---|---|---|
| 9 | 4 | 19 | 10.67 |

Example 5 Effect of H-473 on Asthma in Mice 5.1 Test Samples:

Peptide H-473.

Positive drug: dexamethasone, Zhejiang Xianju Pharmaceutical Co., Ltd., China, batch number: 150921.

5.2 Main reagents:

Ovalbumin, Sigma, Lot SLBK7542V.

Adjuvant liquid aluminum, Thermo, Lot RB231380B.

5.3 Main Instruments:

Compressed air atomizer, Huangshan Yashi Medical Equipment Co., Ltd., China, YS-01.

Blood analyzer, Shandong Hengtuo Technology Development Co., Ltd., China, BTX-1800.

5.4 Test Animals:

Source, germline, and strain: BALB/C mice, provided by Shanghai Sippr-BK Laboratory Animal Co., Ltd., China.

Laboratory animal production license: SCXK (HU) 2013-0016.

Laboratory animal use license: SYXK (SU) 2012-0047.

Body weight: 18-22 g.

Gender: female.

Number of animals: 40.

5.3 Grouping, Modes and Cycles of Administration

Grouping, modes and cycles of administration are shown in Table 4. At day 35 of the experiment, the test samples were respectively given one hour prior to OVA atomization.

TABLE 4

Grouping, modes and cycles of administration

| Group | Mode of administration | Dosage (mg/Kg) | Cycle of administration | Frequency of administration |
|---|---|---|---|---|
| Normal control group | Intramuscular injection | — | 7 d | 1 |
| Model control group | Intramuscular injection | — | 7 d | 1 |
| Positive control group | Intramuscular injection | 1 mg/kg | 7 d | 1 |
| H-473 low-dose group | Intramuscular injection | 15 μg/kg | 7 d | 1 |
| H-473 high-dose group | Intramuscular injection | 30 μg/kg | 7 d | 1 |

5.6 Experimental Method:

5.6.1 Asthma model: mice were injected intraperitoneally with 0.2 ml of a sensitizing solution (ovalbumin OVA 80 μg+ Adjuvant liquid aluminum 0.1 ml) twice on days 0 and 14. From day 24 after the first sensitization, 2.5% OVA was aerosolized and inhaled for 45 min once daily for 18 days.

5.6.2 Administration: the corresponding test sample was given 1 h before the OVA solution atomization challenge since day 35 of the experiment. H-473 15 μg/kg group and H-473 30 μg/kg group were injected intramuscularly, respectively. The positive control group was injected with dexamethasone 1 mg/kg intramuscularly. Normal control group and model control group were injected with saline intramuscularly.

5.6.3 Index Detection and Sampling:

General global observations: respiratory rate, whether there was dyspnea, cyanosis, dysphoria and convulsion.

Bronchoalveolar lavage fluid (BALF) cells were counted and classified (EOS ratio elevated or not).

Mouse serum: 24 hours after the last challenge, blood was collected from mouse eyeballs and centrifuged, and serum was collected.

Lung tissue was fixed in half and frozen in half 5.7 Experimental Results 5.7.1 General Observations:

32 days after the first sensitization, that is, 11 days after atomization, the mice in each group developed dysphoria, nodding breathing, and scratching their noses. 18 days after atomization, the model group showed dyspnea, dysphoria and other reactions, the positive group did not show abnormal reactions, the other administration groups showed the same symptoms as 8 days after atomization, without aggravating trend.

5.7.2 BALF Cell Count and Classification (Table 5)

TABLE 5

BALF cell count and classification (M ± SD, N = 6, $10^9$/L)

| Group | WBC | ESO | ESO % |
|---|---|---|---|
| Normal control group | 1.8 ± 1.0 | 0.04 ± 0.04 | 1.72 ± 0.98 |
| Model control group | 16.3 ± 3.3** | 1.34 ± 0.27** | 8.33 ± 1.26** |
| Positive control group | 3.8 ± 0.5## | 0.15 ± 0.05## | 3.75 ± 0.83## |
| H-473 30 μg/kg | 8.8 ± 1.0## | 0.40 ± 0.07## | 4.60 ± 0.94## |
| H-473 15 μg/kg | 10.4 ± 0.8## | 0.61 ± 0.06## | 5.81 ± 0.56## |

Conclusion: H-473 has remarkable anti-asthma activity.

Example 6 Evaluation of Efficacy of H-473 as an Analgesic 6.1 Experimental Objective:

To observe an analgesic effect of H-473 on mice.

6.2 Test Sample:

Drug Name: H-473.

Preparation method: the test sample was stored at −20° C., and an appropriate amount of the test sample was dissolved with physiological saline to the desired concentration.

6.3 Groups and Dosage Regimen:

Model group: physiological saline, injected intramuscularly, 5 ml/kg.

H-473-L group: H-473, injected intramuscularly, 0.5 mg/kg, once.

H-473-H group: H-473, injected intramuscularly, 1 mg/kg, once.

6.4 Test Animals:

Source, germline, and strain: ICR mouse, provided by Shanghai Lingchang Biotechnology Co., Ltd., China.

Laboratory animal production license: SCXK (HU) 2013-0018, certificate number: 2013001834301.

Laboratory animal use license: SYXK (Su) 2017-0015.

Day age: 5-6 W.

Body weight: 180-220 g.

Gender: female.

Number of animals: 24.

6.5 Experimental Method:

6.5.1 Preparation of Model

According to pharmacological experiment methodology, mice were reared adaptively for 3 days, and then randomly divided into 3 groups according to the group, each with 8 animals. According to the dosage regimen, mice in each group were injected intramuscularly with test samples. One hour after the administration, mice were injected intraperitoneally with 0.2 ml of 2% glacial acetic acid. The number of writhing response (abdominal contraction into an "S" shape, body twisting, hind limb extension and creeping, etc.) of mice were observed within 15 min, and writhing inhibition rate was calculated. Writhing inhibition rate %=(mean number of writhing in control group-mean number of writhing in dosing group)/mean number of writhing in control group×100%.

6.5.2 Statistical Processing

Mean values were expressed as X±SD, inter-group analysis was statistically processed using t-test, and results were statistically analyzed using SPSS (Staffstical Package for the Social Science) 17.0.

6.6 Experimental Results:

As shown in Table 6, H-473 significantly reduced the number of acetic acid-induced writhing response in mice, and each dose group had a significant analgesic effect on acetic acid-induced pain, which was significantly different from the blank control group ($p<0.01$).

TABLE 6

Effect of H-473 on acetic acid-induced writhing response in mice ($X \pm SD$, $n = 8$)

| Group | Dosage (mg/kg) | Mode of administration | n | Number of twists | Inhibition (%) |
| --- | --- | --- | --- | --- | --- |
| Model control group | — | i.m. | 8 | 33.3 ± 4.9 | — |
| H-473 | 0.5 mg/kg | i.m. | 8 | 6.0 ± 3.2** | 81.95% |
| H-473 | 1 mg/kg | i.m. | 8 | 1.6 ± 0.7** | 95.11% |

Example 7 Anti-Psoriatic Drug Experiment 7.1 The latest research results on psoriasis: On Jul. 3, 2018, an article entitled "Gain of function mutation of Card14 leads to spontaneous psoriasis-like skin inflammation through enhanced keratinocyte response to interleukin-17A" was published online by Lin Xin's laboratory of Tsinghua University in Immunity, sub journal of Cell. This paper reports the histopathological phenotypes and inflammatory response types of Card14E138A/+ spontaneous psoriatic mice, and elucidates a molecular mechanism that deletion or mutation of Card14 gene affects the activation of IL-17A signal in keratinocytes, as well as an important role of keratinocytes in the initiation of psoriasis.

At present, the cause of psoriasis is unclear. Recent GWAS studies have shown that there are many mutations in NF-κB signal-related genes in patients with psoriasis, such as CARD14 gene highly expressed in skin. This finding suggests that CARD14 gene may play an important role in a process of inducing psoriasis. CARD14 gene encodes a signal transduction-related protein CARMA2 in cells. Lin Xin's laboratory has been studying functions of CARD family-encoded proteins in immune and inflammatory responses for many years, and explored whether the activation of CARMA2 can induce psoriasis and how to induce psoriasis in this study by constructing a Card14 mutant mouse model.

It was found that CARMA2 is an important regulatory protein of IL-17A signaling pathway in keratinocytes, and its sustained activation in keratinocytes can induce psoriasis. This provides a new direction for the treatment of psoriasis. More importantly, Card14E138A/+ mice can serve as an appropriate model for psoriasis studies, particularly initial stage mechanism studies, as well as a model for therapeutic drug screening and validation.

7.2 Design of Innovative Anti-Psoriasis Drugs

The inventors designed a novel anti-psoriasis peptide small molecule drug from the molecular level according to the action mechanism of existing drugs and the latest research progress.

The design idea is as follows: the designed peptide small molecule drug can effectively interfere TCR, BCR, IL1-R, TNF-R1 and other receptors to bind with pathogenic factors, down-regulate expression level of CARMA through related signal cascade pathway, further inhibit expression of VEGF, achieve a purpose of inhibiting vascular proliferation, and control occurrence and development of psoriasis.

The designed peptide small molecule drug can effectively inhibit IL17RA, NOTCH1-3, CD4, IL4R, CD58, CD2 and other receptors to bind with related cytokines, down-regulate expression level of VEGF and expression of inflammatory factors such as IL12, IL12R, IL1R, IL6, IL8 and the like through cell-related signaling pathways, and control occurrence and development of psoriasis.

7.3 Initial Experiment Results:

7.3.1 Experiment Results at the Molecular Level

H-473, as the peptide small molecule drug, could efficiently bind to TCR, BCR, IL1-R, TNF-R1, IL17RA, NOTCH1-3, CD4, IL12, IL12R, CD58 and CD2 at the molecular level.

7.3.2 Experiment Results at the Cellular Level

H-473, as the peptide small molecule drug, was applied to cultured T and B cells, respectively. Expression levels of related proteins in the cells were detected by ELISA. The results showed that the expression levels of CARMA, VEGF, IL6, IL8, IL1-R, TNF-R1, IL17RA, IL12, IL12R and other proteins were significantly down-regulated.

7.3.3 Experiment Results at the Animal Level

After 12 days of administration of H-473, as the peptide small molecule drug, to experimental mice through muscle and nasal mucosa, the corresponding tissues of animals in model group and experimental group were collected to construct gene pools, and then gene transcription analysis was performed. The results showed that the transcription levels of CARMA, VEGF, IL6, IL8, IL1-R, TNF-R1, IL17RA, IL12, IL12R and other genes were significantly down-regulated.

The experimental results show that H-473, as the peptide small molecule drug, has achieved the expected design purpose, and is expected to be a potent anti-psoriasis drug.

Example 8 Experiment of Small Molecule Peptide Drug Against Age-Related Macular Degeneration (AMD)

8.1 Design of Small Molecule Peptide Drug Against Age-Related Macular Degeneration (AMD)

The small molecule peptide drug was designed based on existing pharmacological principles of several antibodies against age-related macular degeneration (AMD), and further to overcome the main side effects of existing VEGF inhibitors, such as those caused by injection, including conjunctival hemorrhage, acute intraocular pressure rise, traumatic cataract, uveitis, retinal detachment and the like; as well as infections and endophthalmitis that may be caused by injection of VEGF inhibitors, and side effects such as endophthalmitis and blindness in some patients taking bevacizumab without proper aseptic technique.

The design idea is as follows: the designed small molecule peptide drug can: 1. significantly down-regulate VEGF expression in cells; 2. effectively inhibit biological activity of VEGF; 3. effectively interfere with VEGF related receptors such as VEGFR, PDGFR, etc.; and finally inhibit vascular proliferation and achieve a purpose of anti-age-related macular degeneration (AMD).

8.2. Initial Experiment Results:

8.2.1 Experiment Results at the Molecular Level

H-473, as the small molecule peptide drug, could fully bind to VEGF molecule in vitro, as well as related receptor molecules of VEGFR, PDGFR and GF. Theoretically, H-473 can both inactivate VEGF molecule, but also make VEGF molecule lose the opportunity to bind to related receptors.

8.2.2 Experiment Results at the Cell Level

H-473, as the small molecule peptide drug, was applied to cultured lung cancer A549 cells and gastric cancer MGC-803 cells, respectively. Expression levels of related proteins in the cells were detected by ELISA. The results showed that the expression level of VEGF protein was significantly down-regulated.

8.2.3 Experiment Results at the Animal Level

After 15 days of administration of H-473, as the peptide small molecule drug, to experimental mice through nasal mucosa, the corresponding tissues of animals in model group and experimental group were collected to construct gene pools, and then gene transcription analysis was performed. The results showed that the transcription levels of VEGF, IL6, IL8, IL1-R, TNF-R1, IL17RA, IL12, IL12R and other genes were significantly down-regulated.

The experimental results show that H-473, as the peptide small molecule drug, has achieved the expected design purpose, and is expected to become a potent anti-age-related macular degeneration (AMD) drug.

While embodiments of the invention have been shown and described, it will be understood by those of ordinary skill in the art that various changes, modifications, substitutions and alterations may be made to these examples without departing from the principles and spirit of the invention. The scope of the invention is defined in the appended claims and their equivalents.

---

---

What is claimed is:

1. An artificially synthesized peptide H-473, wherein the peptide is shown as SEQ ID NO: 1, the peptide has a molecular weight of 827 Da, and a PI of 12.30.

2. A method for treating human gastric cancer or for treating human pancreatic cancer, comprising administering a therapeutically effective amount of the artificially synthesized peptide H-473 of claim 1.

3. A method for treating senile dementia comprising administering a therapeutically effective amount of the artificially synthesized peptide H-473 of claim 1.

4. A method for treating pain comprising administering a therapeutically effective amount of the artificially synthesized peptide H-473 of claim 1.

5. A method for treating asthma comprising administering a therapeutically effective amount of the artificially synthesized peptide H-473 of claim 1.

6. A method for treating psoriasis comprising administering a therapeutically effective amount of the artificially synthesized peptide H-473 of claim 1.

7. A method for treating macular degeneration comprising administering a therapeutically effective amount of the artificially synthesized peptide H-473 of claim 1.

8. The method of claim 7, wherein the macular degeneration is age-related macular degeneration.

9. The method of claim 4, wherein the pain includes burns and scalds, external force injury, frostbite, inflammatory pain, neuropathic injury and pain caused by other reasons.

* * * * *